Figure 1:
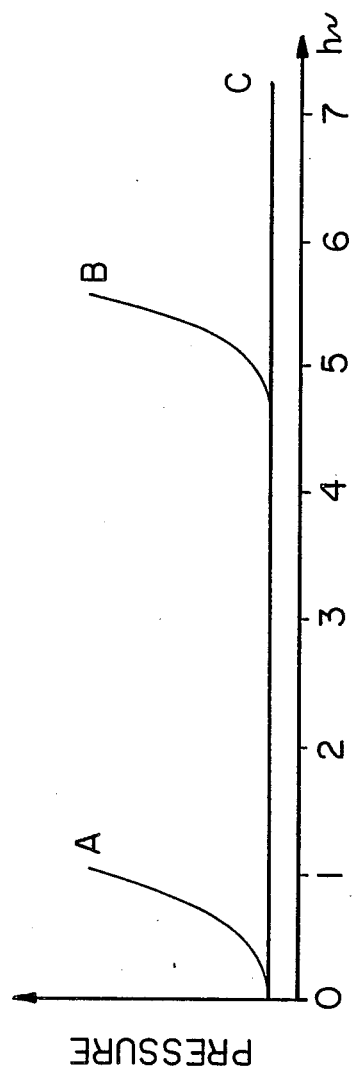

United States Patent [19]

Blum et al.

[11] Patent Number: 4,892,679

[45] Date of Patent: Jan. 9, 1990

[54] OXA-ALKANE POLYPHOSPHONIC ACIDS, THEIR USE AS THRESHOLDERS, AND COMPLEXING COMPOSITIONS CONTAINING THESE COMPOUNDS

[75] Inventors: Helmut Blum, Duesseldorf; Siglinde Hemmann, Meerbusch, both of Fed. Rep. of Germany

[73] Assignee: Henkel Kommanditgeselsschaft auf Aktien, Duesseldorf, Fed. Rep. of Germany

[21] Appl. No.: 314,531

[22] Filed: Feb. 23, 1989

[30] Foreign Application Priority Data

Feb. 24, 1988 [DE] Fed. Rep. of Germany ....... 3805663

[51] Int. Cl.$^4$ .......................... C07F 9/38; A61K 7/16; A61K 31/08; C02F 1/00
[52] U.S. Cl. ...................... 562/21; 210/699; 210/700; 252/389.22; 252/389.23; 424/49; 424/54; 514/76; 514/108
[58] Field of Search ...................... 260/502.4 P, 501.21

[56] References Cited

U.S. PATENT DOCUMENTS

| | | | |
|---|---|---|---|
| 3,833,690 | 9/1974 | Kerst | 260/502.4 P |
| 4,309,364 | 1/1982 | Bentzen et al. | 260/502.4 P |
| 4,624,947 | 11/1986 | Blum et al. | 514/108 |
| 4,732,998 | 3/1988 | Binderup | 260/502.4 P |
| 4,746,654 | 5/1988 | Breliere et al. | 260/502.4 P |

FOREIGN PATENT DOCUMENTS 0039033  4/1981  European Pat. Off.
3434667  9/1984  Fed. Rep. of Germany.

*Primary Examiner*—J. E. Evans
*Attorney, Agent, or Firm*—Ernest G. Szoke; Wayne C. Jaeschke; Henry E. Millson, Jr.

[57] ABSTRACT

Oxa-alkane polyphosphonic acids corresponding to general formula (I)

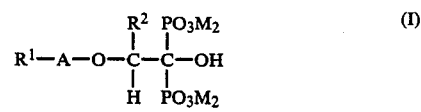

in which
$R^1$ is a $C_1$-$C_{10}$ alkyl group, an optionally substituted $C_6$-$C_{10}$ aryl group, a phenyl- or naphthylalkyl group, a group having the general formula

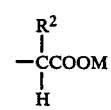

or a group having the general formula

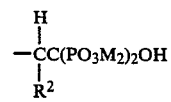

$R^2$ represents H or methyl,
A represents the structural unit

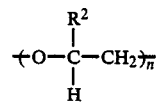

where n is an integer of from 1 to 20 and
M represents H or the cation of a base, to the use of the above compounds as complexing agents and as thresholders, and to compositions containing one or more compounds of general formula (I).

7 Claims, 1 Drawing Sheet

OXA-ALKANE POLYPHOSPHONIC ACIDS, THEIR USE AS THRESHOLDERS, AND COMPLEXING COMPOSITIONS CONTAINING THESE COMPOUNDS

BACKGROUND OF THE INVENTION

1. Field of the Invention

This invention relates to oxa-alkane polyphosphonic acids and salts thereof, to their use as thresholders, and to complexing compositions containing these oxa-alkane polyphosphonic acid derivatives.

2. Statement of Related Art

It is known from published German application no. 34 34 667 that 4-dimethylamino-1-hydroxybutane-1,1-diphosphonic acid can be prepared by phosphonylation from 4-dimethylaminobutyric acid hydrochloride.

In addition, it is known from European Patent No. 39 033 that $\omega$-amino-1-hydroxyalkylidene-1,1-bisphosphonic acids can be prepared by phosphonylation from $\omega$-aminocarboxylic acids. Both products show complexing and threshold-active properties.

In view of the increasing pollution of waters by ethylenediamine tetraacetic acid (EDTA), the search for suitable substitutes has become an acute problem. The poor biodegradability of EDTA is a particularly troublesome disadvantage. Since, in contrast to most phosphonate complexing agents, EDTA does not show any threshold activity, it has to be used in stoichiometric quantities for adequate complexing in numerous industrial processes where scaling occurs under the effect of the hardness elements in water. In many cases, therefore, EDTA is replaced by the structural analog, ethylenediamine tetramethylene phosphonic acid (EDMP), which shows the desired threshold effect. However, like most other complexing and threshold-active phosphonates, EDMP is also attended by the disadvantage of poor biodegradability.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide organic phosphonic acid derivatives which show excellent threshold activity and complexing properties as well as better biodegradability.

This object is achieved by new oxa-alkane polyphosphonic acids.

The present invention relates to oxa-alkane polyphosphonic acids and basic addition salts thereof corresponding to general formula (I)

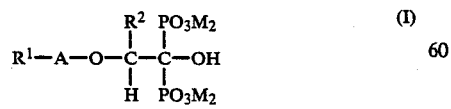

in which

R$^1$ is a straight or branched chain $C_1$–$C_{10}$ alkyl group, an optionally substituted $C_6$–$C_{10}$ aryl group, a phenylalkyl or napthylalkyl group, a group having the general formula

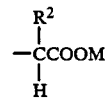

or a group having the following general formula

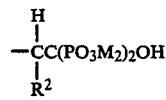

R$^2$ is H or methyl,
A represents the structural unit

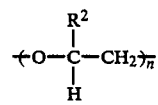

where n is an integer of from 1 to 20, and
M represents H or the monovalent cation of a base.

The oxa-alkane polyphosphonic acids according to the invention have the advantage of pronounced threshold activity, so that they may be added in smaller seed quantities than usual in order to completely inhibit the precipitation of, for example, calcium sulfate and calcium carbonate. This is also an ecological advantage because smaller quantities of phosphorus are introduced into the environment for the same seeding performance. This is particularly advantageous in cases where the substances are used as sequestrants and, hence, in relatively large quantities. Finally, by virtue of the oxygen bridges, these chelating agents will show better biodegradability. Complexing phosphonates containing pure carbon bridges, as in EDMP, or alkyl groups are known to show poor biodegradability.

The present invention also relates to the use of the compounds corresponding to general formula (I) as complexing agents and as thresholders.

The invention also relates to compositions containing one or more compounds corresponding to general formula (I) in complexing concentrations.

Oxa-alkane polyphosphonic acids of formula I include both oxa-alkane diphosphonic acids and also oxa-alkane tetraphosphonic acids.

In the compounds of formula (I), R$^1$ is preferably a $C_1$–$C_4$ alkyl group, such as methyl, ethyl, propyl, i-propyl, n-butyl, i-butyl and tert.-butyl, more preferably methyl.

In addition, R$^1$ is preferably a group having the formula

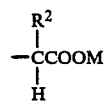

or a group having the following formula

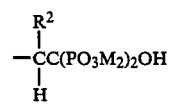

where $R^2$ represents H or a methyl group. Where $R^1$ represents an optionally substituted aryl group, the aryl group is phenyl or naphthyl. Substituents that can be present on the aryl group include one or more $C_1$–$C_4$ alkyl groups, and/or halogen groups, e.g. chlorine or bromine. Where $R^1$ is a phenyl- or naphthyl-alkyl group, the alkyl moiety is a $C_1$–$C_4$ alkyl group, and is preferably benzyl.

In the compounds of general formula (I), in A, the multiplicator n of the structural unit

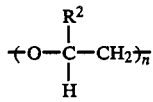

is preferably an integer of from 1 to 12; more preferably, n=1, 2, 10, 11, or 12.

Preferred oxa-alkane diphosphonic acids are 3,6-dioxaheptane-1-hydroxy-1,1-diphosphonic acid, 3,6,9-trioxadecane-1-hydroxy-1,1-diphosphonic acid, 3,6,9-trioxaundecane-11-carboxy-1-hydroxy-1,1-diphosphonic acid, and polyglycol-ω-carboxy-1-hydroxy-1,1-diphosphonic acid.

Preferred oxa-alkane tetraphosphonic acids are 3,6,9-trioxa-1,11-dihydroxyundecane-1,1,11,11-tetraphosphonic acid and α,ω-dihydroxypolyglycol-α,α,ωω-tetraphosphonic acid.

Preferred complexing compounds corresponding to general formula (I) above are those in which M, instead of the proton for the free acids, represents alkali metal cations or an ammonium cation having the general formula $R^3R^4R^5R^6N^+$. A major advantage of these salts derived from the free acids is that they clearly improve the solubility of the free acids (M=H) of compounds of formula (I) in water which, of course, also improves the useability of such compounds in compositions which have a threshold effect. Alkali metal cations are preferably $Na^+$ or $K^+$. However, M can also represent ammonium cations having the above general formula, in which and $R^3$, $R^4$, $R^5$ and $R^6$ independently of one another represent hydrogen or branched or unbranched alkyl radicals containing from 1 to 12 carbon atoms. Accordingly, such alkyl radicals include any branched and unbranched methyl, ethyl, propyl, butyl, pentyl, hexyl, heptyl, octyl, nonyl, decyl, undecyl and dodecyl radicals.

According to the invention, preferred water-soluble salts are the alkali metal salts of general formula (I) in which M is an alkali metal cation. The sodium salts are particularly preferred. Partial salts are also included within the scope of the invention, i.e. where one or more, but not all, M groups are hydrogen and the other M group or groups are a monovalent cation. However, salts where all M groups represent a monovalent cation are preferred.

The compounds corresponding to general formula (I) are prepared by reaction of oxa-alkyl carboxylic acids of formula (II)

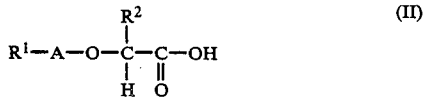

in which A and $R^2$ are as defined above, and $R^1$ is a $C_1$–$C_{10}$ alkyl group, an optionally substituted $C_6$–$C_{10}$ aryl group, a phenylalkyl or naphthylalkyl group, or a group having the general formula

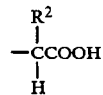

with excess phosphonylating agents, such as phosphorous acid, in the presence of phosphoryl chloride. Where oxa-alkyl dicarboxylic acids are used as starting materials, oxa-alkane diphosphonic acids are mainly obtained if the phosphonylating agent is used in a stoichiometric quantity, whereas oxa-alkane tetraphosphonic acids are mainly obtained if the phosphonylating agent is used in twice the stoichiometric quantity.

The starting materials used are generally known from the literature or may be prepared by those skilled in the art analogously to the known starting materials.

It has surprisingly been found that the compounds of general formula (I) show excellent complexing properties with respect to alkaline earth ions, particularly calcium ions.

In addition to their excellent complexing power, the compounds of general formula (I) are distinguished by strong threshold activity, i.e. they are capable of preventing the precipitation of poorly soluble alkaline earth metal salts when used even in seed quantities, i.e. in substoichiometric quantities.

They can be widely used as complexing agents. For example, they can be used in the softening of water, in which case the threshold effect discussed above is a crucial factor. Accordingly, there is no need to use stoichiometric quantities, because precipitations of poorly soluble calcium salts can be considerably retarded even with substoichiometric quantities.

They are also eminently suitable for use as corrosion inhibitors and scale inhibitors for cooling waters, particularly in combination with additives known for this use.

To this end, one or more compounds corresponding to general formula (I) are preferably used in quantities of from 1 to 50 mg/l in compositions used as thresholders against scale-forming salts. Compositions containing one or more compounds corresponding to general formula (I), in which $R^1$, $R^2$, A and n are as defined above and M is an alkali metal cation, preferably a sodium ion, in concentrations of from 1 to 20 mg/l are particularly effective in this respect.

Compositions of this type are particularly suitable for preventing the deposition of scale-forming salts, even at very high scale-forming concentrations. To this end, they need only be used in a comparatively low concentration which makes them distinctly superior to other structurally comparable complexing compositions.

The compounds of general formula (I) are also useful for pharmaceutical purposes in the treatment of animal disorders of the calcium or phosphate metabolism and the diseases associated therewith, e.g. in daily dosages of from 1 to 30 mg/kg body weight. The compounds according to the invention can also be used in cosmetic preparations, including dental and oral hygiene preparations, for example mouth rinses, toothpowders, tooth creams or toothpastes, mouthwashes and dental fixatives and for the treatment and prophylaxis of calculus. The compounds according to the invention can also be used in conjunction with technetium-99m for skeletal scintigraphy.

The invention is illustrated but not limited to the following Examples.

EXAMPLES

EXAMPLE 1

0.5 mol 3,6,9-trioxadecanoic acid was added dropwise to a mixture of 1 mol phosphonic acid and 1 mol phosphoryl chloride, a slight exothermic reaction occurring. The resulting reaction mixture was stirred for 10 hr at 55° C. The reaction product was then hydrolyzed and the hydrochloric acid formed was removed by concentration in a rotary evaporator. For separation of phosphate, the concentrated reaction mixture was adjusted to a pH value of 8.8. The disodium phosphate crystallized out was separated off and the reaction product was converted into the solid form after pH adjustment by addition of acetone. An aqueous trisodium salt of 3,6,9-trioxa-1-hydroxydecane-1,1-diphosphonic acid (compound 1) was isolated in this way in a yield of 77%.

| Elemental analysis | P | C | Na |
|---|---|---|---|
| Found | 2.00 | 6.9 | 3.2 |
| Calculated | 2 | 7 | 3 |

Molecular weight of a dehydrated sample as calculated from acid-base titration: 392.3 after consumption of two equivalents and 393.4 after consumption of three equivalents alkali (theoretical 390).

EXAMPLE 2

0.25 mol 3,6,9-trioxaundecane-1,11-dioic acid was added dropwise to a phosphonylating reagent of 1 mol phosphonic acid and 1 mol phosphoryl chloride, followed by heating for 18 h at 55°–60° C. After hydrolysis and concentration, disodium phosphate was separated off by pH adjustment to 8.8 and crystallization. The heptasodium salt of 3,6,9-trioxa-1,11-dihydroxyundecane-1,1,11,11-tetraphosphonic acid (compound 2) was obtained in solid, water-containing form by precipitation with methanol. Yield: 52%.

| Elemental analysis | P | C | Na |
|---|---|---|---|
| Found | 4.00 | 7.89 | 7.08 |
| Calculated | 4 | 8 | 7 |

EXAMPLE 3

The tetrasodium salt of 3,6,9-trioxa-1,1-diphosphono-1-hydroxyundecanoic acid (compound 3) was obtained by addition of 0.5 mol 3,6,9-trioxaundecane-1,11-dioic acid to the phosphonylating agent of Example 2 after heating for 10 hours at 55° to 60° C. and working up in the same way. Yield: 58%.

| Elemental analysis | P | C | Na |
|---|---|---|---|
| Found | 2.00 | 8.17 | 4.23 |
| Calculated | 2 | 8 | 4 |

EXAMPLE 4

To determine seeding performance with respect to the formation of gypsum scale, a saline test water having the composition shown below was pumped through a 1 meter long steel capillary with an internal diameter of 1 mm by a piston lift pump in a flow test simulating practical conditions. The throughflow was 500 ml per hour. The steel capillary was monitored by a thermostat. The measurement was performed at 70° or 90° C. When scale is deposited, the internal diameter becomes smaller, producing an increase in pressure which is recorded. The pressure recording instrument was situated between the piston lift pump and the measuring capillary. When a pressure of approximately 0.552 bar (8 psi) was reached, the pump was automatically switched off. The curves obtained, which show the advantageous property of the oxa-alkane phosphonic acids according to the invention by comparison with EDMP, are shown in FIG. 1 where the letters used have the following meanings: A=blank value, B=EDMP for comparison, C=oxa-alkane polyphosphonic acids obtained in accordance with Examples 1 to 3.

Test conditions:
Scale-forming concentration: 8,000 mg CaSO4/l
Temperature: 70° C.
Electrolyte concentration: 14,000 mg NaCl/l
pH value of the salt solution: 6.4 to 6.6
Seed concentration: 5 ppm

EXAMPLE 5

To determine sequestering performance, the soda-alkaline oxa-alkane polyphosphonate solution adjusted to pH 11 was titrated with a calcium chloride solution until calcium carbonate was precipitated. The values observed are shown below in mg $CaCO_3$ per mg-atom phosphorus. They show that the sequestering performance, based on the quantity of P used, of the oxa-alkane polyphosphonic acids is greater than that of the comparison substance, EDMP.

| Sequestering performance in mg $CaCO_3$/mg-atom P | |
|---|---|
| EDMP | 109 |
| Compound 1 | 133 |
| Compound 3 | 156 |

We claim:

1. An axo-alkane polyphosphonic acid or basic addition salt thereof of the formula:

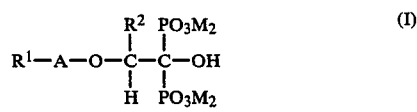

in which

R$^1$ is a straight or branched chain C$_1$–C$_{10}$ alkyl group, an unsubstituted or substituted C$_6$–C$_{10}$ aryl group, a phenylalkyl or napthylalkyl group, a group having the formula

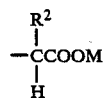

or a group having the formula

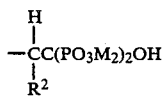

R² is H or methyl,
A is the structural unit

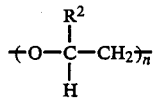

where n is an integer of from 1 to 20, and
M is H or the monovalent cation of a base.

2. A compound of claim 1 wherein $R^1$ is a $C_1$–$C_4$ alkyl group, a group having the formula

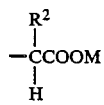

or a group having the formula

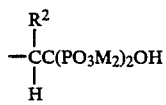

n in structural unit A is an integer of 1 to 12; and M is a monovalent cation of a water-soluble base.

3. A compound of claim 1 wherein $R^1$ is a methyl group, a group having the formula

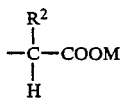

or a group having the formula

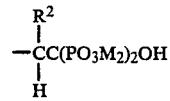

and n in structural unit A is the number 1, 2, 10, 11, or 12.

4. A compound of claim 1 wherein M is an alkali metal cation or an ammonium cation having the formula $R^3R^4R^5R^6N^+$, in which $R^3$, $R^4$, $R^5$ and $R^6$ independently of one another represent hydrogen or an unbranched or branched alkyl radical containing 1 to 12 carbon atoms.

5. A compound of claim 2 wherein M is an alkali metal cation or an ammonium cation having the formula $R^3R^4R^5R^6N^+$, in which $R^3$, $R^4$, $R^5$, and $R^6$ independently of one another represent hydrogen or an unbranched or branched alkyl radical containing 1 to 12 carbon atoms.

6. A compound of claim 3 wherein M is an alkali metal cation, or an ammonium cation having the formula $R^3R^4R^5R^6N^+$, in which $R^3$, $R^4$, $R^5$ and $R^6$ independently of one another represent hydrogen or an unbranched or branched alkyl radical containing 1 to 12 carbon atoms.

7. A compound of claim 1 wherein M is a sodium ion.

* * * * *